United States Patent
Ecker et al.

(10) Patent No.: US 7,824,385 B2
(45) Date of Patent: Nov. 2, 2010

(54) SANITARY ARTICLE INCLUDING INK USED TO INCREASE THE HYDROPHOBICITY OF AN AREA OF THE ARTICLE

(75) Inventors: Cornelia Ecker, Schwalbach (DE); Ivano Gagliardi, Pescara (IT); Vincenzo Partenza, Elice (DE); Paolo Veglio, Pescara (IT)

(73) Assignee: The Procter & Gamble Company, Cincinnati, OH (US)

( * ) Notice: Subject to any disclaimer, the term of this patent is extended or adjusted under 35 U.S.C. 154(b) by 868 days.

(21) Appl. No.: 11/584,094

(22) Filed: Oct. 20, 2006

(65) Prior Publication Data

US 2007/0093770 A1    Apr. 26, 2007

(51) Int. Cl.
*A61F 13/15* (2006.01)
(52) U.S. Cl. ............... 604/385.01; 604/361; 604/366; 604/385.28
(58) Field of Classification Search ............... 604/361, 604/367, 385.28, 366, 385.01; 116/200, 116/206, 207
See application file for complete search history.

(56) References Cited

U.S. PATENT DOCUMENTS

| 4,015,604 | A | 4/1977 | Csillag |
| 5,817,079 | A | 10/1998 | Bergquist et al. |
| 2003/0171729 | A1* | 9/2003 | Kaun et al. ............... 604/382 |
| 2004/0015145 | A1* | 1/2004 | Miura et al. ............... 604/367 |
| 2005/0096614 | A1 | 5/2005 | Perez et al. |

FOREIGN PATENT DOCUMENTS

| EP | 1 579 831 A1 | 9/2005 |
| WO | WO 91/19471 | 12/1991 |

OTHER PUBLICATIONS

European Search Report dated May 30, 2006.

* cited by examiner

*Primary Examiner* — Jacqueline F. Stephens
(74) *Attorney, Agent, or Firm* — Amanda T. Barry; David M. Weirich (57) ABSTRACT

Sanitary articles such as sanitary napkins including several layers, wherein an ink is applied on at least one of the layers. The ink application area is situated at least partially above the core and extends outwardly across at least a portion of the periphery of the core, but does not entirely cover the core. The ink is visible in the finished article. The ink provides improved resistance to re-wet of the topsheet and side leakage of the core.

14 Claims, 9 Drawing Sheets

SANITARY ARTICLE INCLUDING INK USED TO INCREASE THE HYDROPHOBICITY OF AN AREA OF THE ARTICLE

FIELD OF THE INVENTION

The invention relates to absorbent sanitary articles, in particular disposable sanitary napkins, comprising an ink applied on a specific area of one of the layers making the article in order to increase the hydrophobicity of the area of application.

BACKGROUND OF THE INVENTION

Absorbent sanitary articles are used to collect various bodily fluids for hygiene purposes. For example, sanitary napkins are normally used by women during their menstrual periods to receive and contain blood discharges from the vagina. These articles are normally placed between the user's crotch and her undergarment. In addition to collecting menses, absorbent sanitary articles may also be used to protect the wearer's undergarment from other body fluid such as urine in the case of incontinence of the user.

Absorbent sanitary articles are generally built around a core containing an absorbent material (often a dried hydrogel) enclosed within a liquid pervious topsheet (skin-facing) and a backsheet (garment facing). In addition, other layers such as a secondary topsheet (STS) or lateral topsheet stripes (LTS) can also be built in the article to further improve its properties. The absorbent material within the core can theoretically trap relatively large amount of bodily fluids until saturation, however the user will normally change the article well before saturation for fear of premature failure of the article. One of the most common failures encountered is the leakage of previously absorbed fluid through the lateral sides of the article. Another common failure is the re-wetting of topsheet of the article by fluids previously absorbed within the core, which may happen when the wearer's movements subject the article to stress. In case of re-wet, the soiling of the longitudinal edges may also happen via the topsheet or STS if present.

It has been proposed in the past to use moisture indicators disposed along the side edges of the core to give early warning to the user of an imminent side leakage (WO91/19471). Whilst this system may improve the confidence of the user in the product, it however does not prevent the leakage itself and can be relatively costly and complicated to integrate in existing sanitary articles.

It has also been proposed, among other solutions, to increase the leakage resistance of the core by mixing fluid repellent fibers and fluid absorbent fibers in discrete area of the core, in particular its periphery (U.S. Pat. No. 5,817,079) or by "sealing" the core with an hydrophobic material (U.S. Pat. No. 4,015,604) or by incorporating a thermoplastic material between the absorbent core and the at least one fluid acquisition/distribution layer (EP1,579,831A1). As with the previous system, these methods suffer from being complicated and costly and have not been adopted by the industry.

Furthermore, improving the leakage resistance of a standard article by conventional, non-visible, means such as increasing the quantity of absorbent material in the core will not necessarily translate into better consumer benefits as the user will not change her pattern of product's usage and will continue to discard the article well before the item is saturated. Furthermore these may be costly.

There is therefore a need for a relatively cheap and simple system to provide sanitary articles with visibly improved resistance to leakage. The inventors have found that applying an ink in an area situated partially above the core and which also extends outwardly across at least a portion of the periphery of the core, can help preventing leakage along that portion of the periphery of the core and re-wetting. A simultaneous benefit is that this ink presents a visual clue to the user that the article has an improved resistance to leakage along that portion of the periphery of the core, e.g. the longitudinal edges. The ink may be relatively cheaply printed using conventional roll printing means on a layer of a standard article without the need to develop a new architecture of the article.

SUMMARY OF THE INVENTION

An absorbent sanitary article made of several layers, including:
a liquid pervious topsheet;
a backsheet, at least partially peripherally joined to the topsheet;
an absorbent core disposed between the topsheet and the backsheet, the absorbent core having a periphery; and
an ink applied to at least one ink application area of one of the layers of the article, such that the hydrophobicity of the area is increased, wherein part of the ink application area is above the core and part extends outwardly across at least a portion of the periphery of the core, but wherein the ink application area does not entirely cover the core, and wherein the ink application area is at least partially visible in the finished article.

BRIEF DESCRIPTION OF THE DRAWINGS

While the specification concludes with claims which particularly point out and distinctly claim the invention, it is believed the present invention will be better understood from the following description of preferred embodiments taken in conjunction with the accompanying drawings, in which like reference numerals identify identical elements and in which:

DETAILED DESCRIPTION OF THE INVENTION

As used herein, the term "absorbent sanitary articles" refers to devices that absorb and contain liquid, and more specifically, refers to devices that are placed against or in proximity to the body of the wearer to absorb and contain the various exudates discharged from the body.

As used herein, the term "feminine hygiene article" refers to disposable absorbent articles to be worn by women for menstrual and/or light incontinence control such as sanitary napkins. Feminine hygiene articles are typically held in place adjacent the user's externally-visible genitalia (i.e., the pubic region) by the user's undergarment. Feminine hygiene articles can be placed into the user's undergarment and affixed via adhesive or other joining means.

Figure 1:
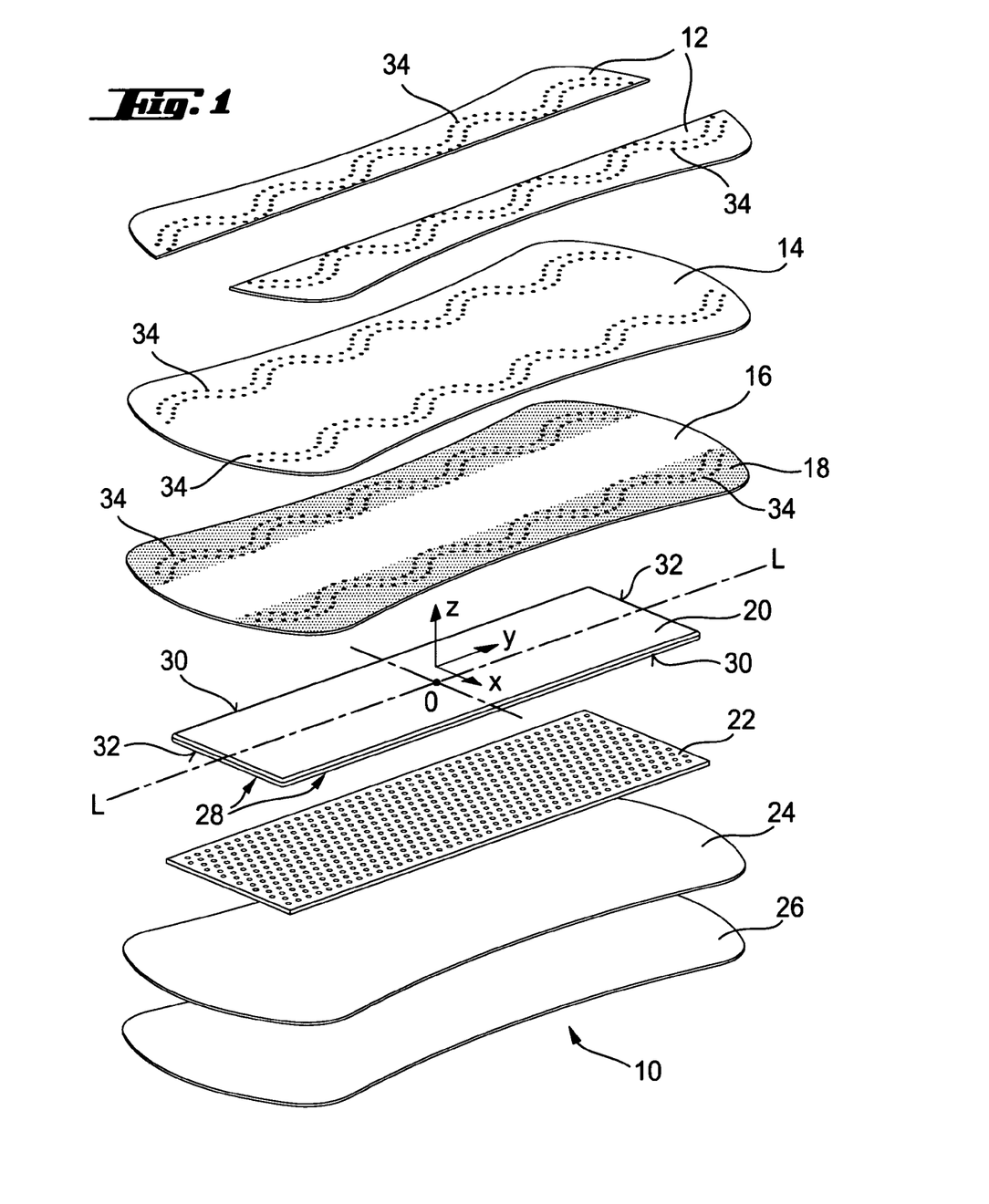
FIG. 1 is an exploded perspective view of a sanitary napkin according to the invention, wherein the ink is applied as two lateral stripes on the secondary topsheet and extend along the longitudinal sides of the core.

Referring now to FIG. 1, a feminine hygiene article 10 is depicted in an exploded view comprising, from top to bottom, the following layers: two lateral topsheet stripes 12, a topsheet 14, a secondary topsheet 16 on which two stripes of ink 18 have been applied, an absorbent core 20, a secondary backsheet 22, a backsheet 24 and releasable wrap 26. The "top" of article is defined herein as the surface of the article contacting the user's body, and the "bottom" is defined herein as the opposite surface of the article, i.e. the woman's undergarment in the case of a feminine hygiene article.

The articles comprise a generally planar absorbent core 20 disposed between the topsheet 14 and the backsheet 24. As used herein, the term "absorbent core" refers to a material or combination of materials suitable for absorbing, distributing, and storing aqueous fluids such as urine, blood, menses, and other body exudates.

The size and shape of the absorbent core can be altered to meet absorbent capacity requirements, and to provide comfort to the wearer. As with the other layers of the article of the invention, there are no particular requirements for the absorbent core and any standard liquid-absorbent material known in the art for use in absorbent articles will normally be suitable.

Non-limiting examples of liquid-absorbent materials suitable for use as the absorbent core include comminuted wood pulp which is generally referred to as airfelt; creped cellulose wadding; absorbent gelling materials including superabsorbent polymers such as hydrogel-forming polymeric gelling agents; chemically stiffened, modified, or cross-linked cellulose fibers; meltblown polymers including co-form; synthetic fibers including crimped polyester fibers; tissue including tissue wraps and tissue laminates; capillary channel fibers; absorbent foams; absorbent sponges; synthetic staple fibers; peat moss; or any equivalent material; or combinations thereof.

The core may be generally planar, i.e. does not have a significant variation in thickness. In embodiments wherein the core is generally planar, the plane is defined by the upper (skin-facing) surface of the core is designated herein as (Oxy).

The periphery 28 of the absorbent core 20 can take various shapes. Typically, as shown in FIG. 1, the absorbent core is rectangularly shaped, for ease of manufacturing. However, the core may be differently shaped, for example there is frequently a wearer preference for an absorbent core which is narrower at the center than at the ends, to comfortably accommodate the legs, and obviate or minimize occurrences of bunching or wadding of the core. Such wearer preference is more frequently encountered when the absorbent core is utilized in conjunction with a sanitary napkin. Oval shaped core have been proposed (e.g. WO2005/084596). Further generic and specific information regarding absorbent cores can be found WO0207662A1 and WO09119471.

Referring back to FIG. 1, the sanitary napkin and absorbent core have a longitudinal centerline LL which conceptually divides the sanitary napkin into two substantially symmetrically opposite halves. As used herein the term "longitudinal" refers to an imaginary line, axis or direction of the absorbent core, which line, axis or direction is typically centered between the longitudinal side margins 30 of the absorbent core and is generally aligned with the vertical plane (0yz) which bisects a standing wearer into left and right body halves. The term "transversal" refers to an imaginary line, axis or direction generally orthogonal the longitudinal direction, within the plane of the absorbent core, and is generally sideways aligned relative to the wearer.

In general, sanitary articles are substantially elongated in the longitudinal direction compared to the transversal direction to conform to human's anatomy. The absorbent core may comprise two longitudinal side edges 30 which may or may not be parallel, and may or may not be straight, and may also comprise two transversal side edges 32 which may or may not be parallel, and may or may not be straight.

Ink 18 can be used in the invention to modify the surface tension properties of the layer of the article on which it is applied so as to increase its hydrophobicity (water-repelling property), once the ink has dried. The level of hydrophobicity of a substrate, with or without ink, can be measured by any standard techniques, for example by measuring the contact angle between a drop of water and the surface of the substrate. An explanation of this method is described in the experimental section below. Conventional hydrophilic or hydrophilically-treated layers (e.g. core or topsheet) may simply absorb the drops of water as they are laid and no contact angle is measurable before application of an hydrophobic composition. The ink should make the area of application of such a surface at least sufficiently hydrophobic so that a contact angle measurement becomes possible.

Many commercial inks are solvent-based (i.e. non-water based) and therefore capable to provide the hydrophobic effect sought. In addition, hydrophobic agents such as oils or waxes may be added to the commercial ink composition if necessary. A "solvent-based" ink does not use water as the mobile phase to carry various pigments, resin(s) or binder(s), and additives, such as wax. Typically, "solvent-based" inks use one or more of various organic solvents such as alcohols, esters, aliphatics, and aromatics to solubilize these components. Solvents that solubilize resins well are generally referred to as "active", while those that are not "active" are called "diluents". A "water-based" ink typically uses water predominantly as the mobile phase. Solvent-based inks that typically use aliphatic hydrocarbons with common binder types, such as polyamide, shellac, rosin esters, nitro-cellulose, and styrene maleic are suitable for use herein. Suitable solvent-based inks include non-catalytic, block urethane resins, which have demonstrated superior durability over traditional flexographic binders, such as styrene-maleic, rosin-maleic, acrylic solutions. Some water-based inks may also suitable for the invention as long as they make the layer of the article on which they are applied more hydrophobic once dry. In the context of the invention solvent-based ink are generally preferred.

Suitable solvent blends include blends ranging in volume up to about 50% of various acetates such as ethyl acetate, N-propyl acetate, isopropyl acetate, isobutyl acetate, N-butyl acetate, and blends thereof; up to about 10% of various alcohols including ethyl alcohol, isopropyl alcohol, normal propyl alcohol, and blends thereof; and up to 75% glycol ethers including Ektasolve® EP (ethylene glycol monopropyl ether), EB (ethylene glycol monobutyl ether), DM to (diethylene glycol monomethyl ether), DP (diethylene glycol monopropyl ether), and PM (propylene glycol monomethyl ether), which can be obtained from; Eastman Chemical, P.O. Box 431, Kingsport, Tenn. 37662. Other suitable solvents can also be obtained from Union Carbide Chemicals, 39 Old Ridgebury Road, Danbury, Conn. 06817. A desired solvent blend is a blend of about 50% to 15 about 75% glycol ether, about 25% to about 35% N-propyl acetate, and about 15% to about 25% N-butyl acetate. Other glycols can be used such as DOWANOL®, obtainable from Dow Chemical, Midland, Mich. 48640.

Examples of suitable inks are supplied by Sunchemical/Hartmann Niederhausen/TS under the trade name P-3228/811 PMS 270 Lavender or trade name V8185/811 PMS 382 Green.

The ink 18 may be applied on at least one of the layer of the article. The ink application area is at least partially above the core, and extends outwardly across at least a portion of the periphery of the core. By "partially above the core", it is meant that part of the ink application area is situated vertically above the core in the finished article. The part of the area situated above the core may be in direct contact with the upper surface of the core, for example when the ink is applied on the secondary topsheet, or not, for example when applied on the topsheet or the lateral stripes, but the ink is normally not applied on the core itself. Having part of the area of application above the core protects from re-wetting in that area, i.e. vertical leakage of the previously absorbed liquid from the core to the skin-facing surface of the article.

Figure 2:
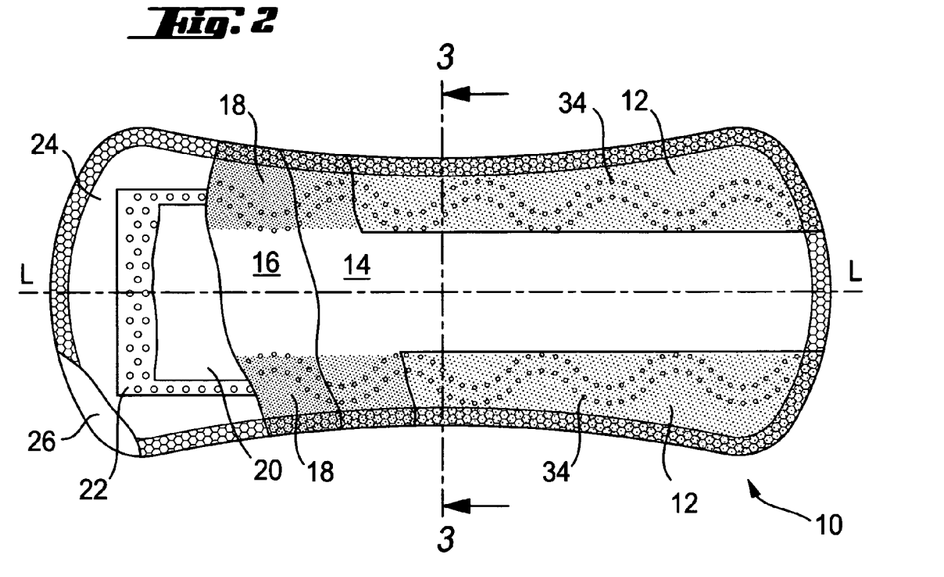
FIG. 2 is a top view, shown partially in cutaway, of the sanitary napkin of FIG. 1.

The area of application extends from the part situated above the core outwardly across at least a portion of the periphery core. The inventors believe that applying an ink according to this configuration creates a barrier effect which helps preventing or slowing leakages from the core to the side of the article. As shown on FIG. 2, the area extending outwardly across the periphery of the core may also extend downwardly, e.g. to join the backsheet or secondary backsheet. The ink application area may also extend horizontally (i.e. in a direction parallel to (Oxy) or upwardly.

Since part of the ink application area is situated above the core, the ink is at least partially applied to a layer situated, at least partially, above the plane (Oxy). For example, the ink may be applied on any of the surfaces (lower or upper) of the topsheet, the secondary topsheet or the lateral topsheet stripes (when these are present), or any other supplementary layers situated above the core.

Figure 4:
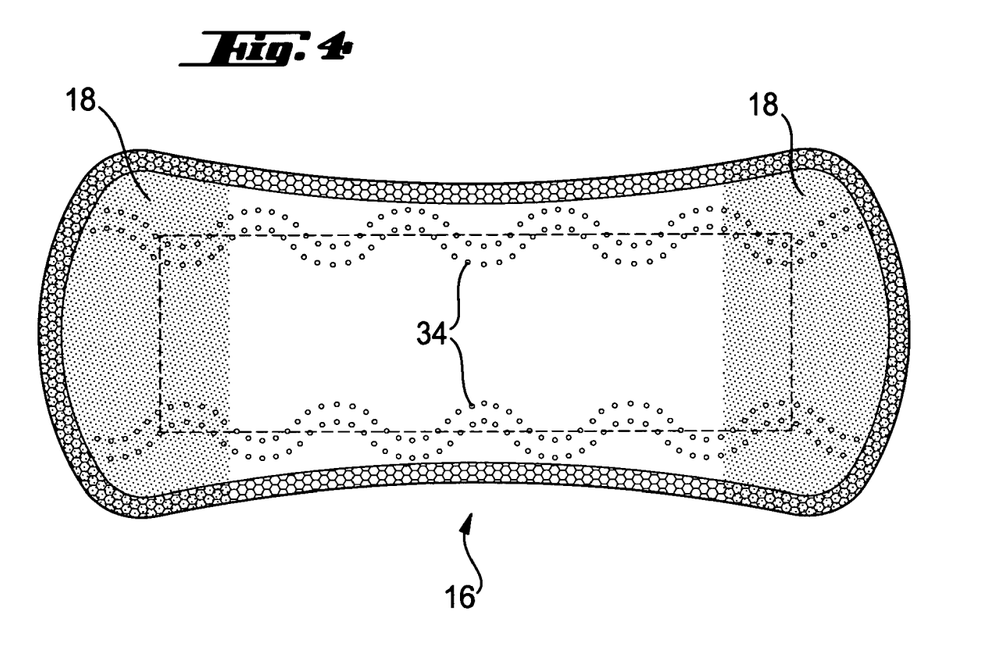
FIG. 4 is a top view of a layer of an article according to the invention (e.g. the secondary topsheet) on which the ink has been applied along the transversal edges.
Figure 5:
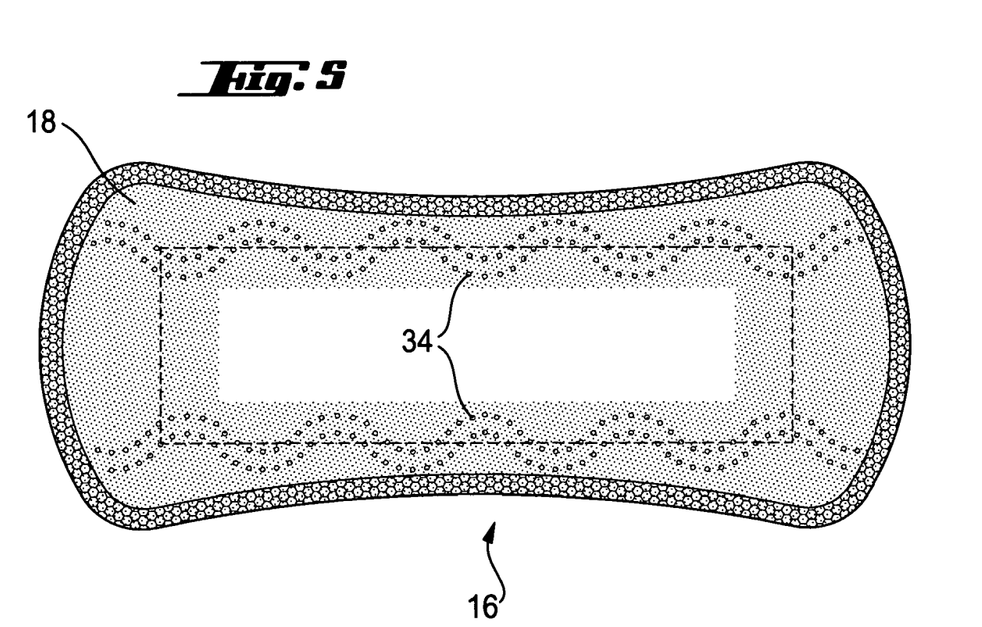
FIG. 5 is a top view of a layer of an article according to the invention (e.g. the secondary topsheet) on which the ink has been applied along the whole of the periphery of the layer.

The ink application area may take different overall shape. In one embodiment, as shown on FIG. 1, the ink application area may take the form of two parallel stripes, which extend substantially along the whole length of the longitudinal sides of the article. In another exemplary embodiment (FIG. 4), the area of application may be two stripes that extend substantially along the whole length of the transversal side edges of the article, or in another embodiment completely surrounds its periphery (FIG. 5). The width of the ink application area may be between about 0.4 cm and about 3 cm, between about 0.5 cm and about 2.5 cm, or larger if desired for the particular application concerned.

Figure 3:
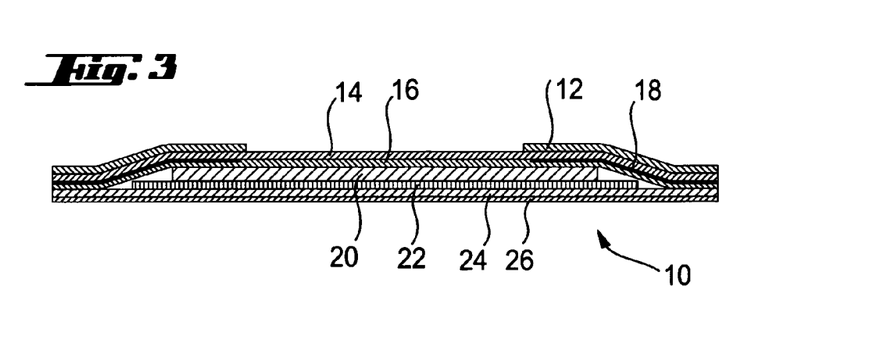
FIG. 3 is a cross-section view taken along line 3-3 of FIG. 2.

The ink application area can extend to the side edge of the article, as is represented in FIGS. 1 and 3, to provide an improved barrier effect.

The ink application area, however, typically does not entirely cover the core, as otherwise the ink could negatively impact the penetration of the bodily fluid within the core. The percentage of the area of the core covered by the ink vs. the total area of the core is typically not zero, but more typically may be at least about 30%, at least about 50% or at least about 60% of the total area of the core.

The ink used may be applied by any conventional means, such as flexo print or roto gravure printing. The ink is released from the gravure roll to the web surface and then the printed web is cured and dried in order to permanently fix the ink on the web surface avoiding any potential smearing or contamination issue. The print roll is engraved according to the desired print coverage and shape of the area of application. The print coverage within the area of application of the ink may be at least about 10%, at least about 25%, at least about 50% and up to about 100%. The hydrophobicity of the ink application area is generally proportional to the percentage of coverage by the ink, so that an area with a lower percentage of coverage typically will be less hydrophobic.

The ink may be applied on any of the layers making the article. In certain embodiments, at least part of the ink application area is situated above the core and part extends outwardly from the core across at least a portion of the periphery of the core.

Figure 6:
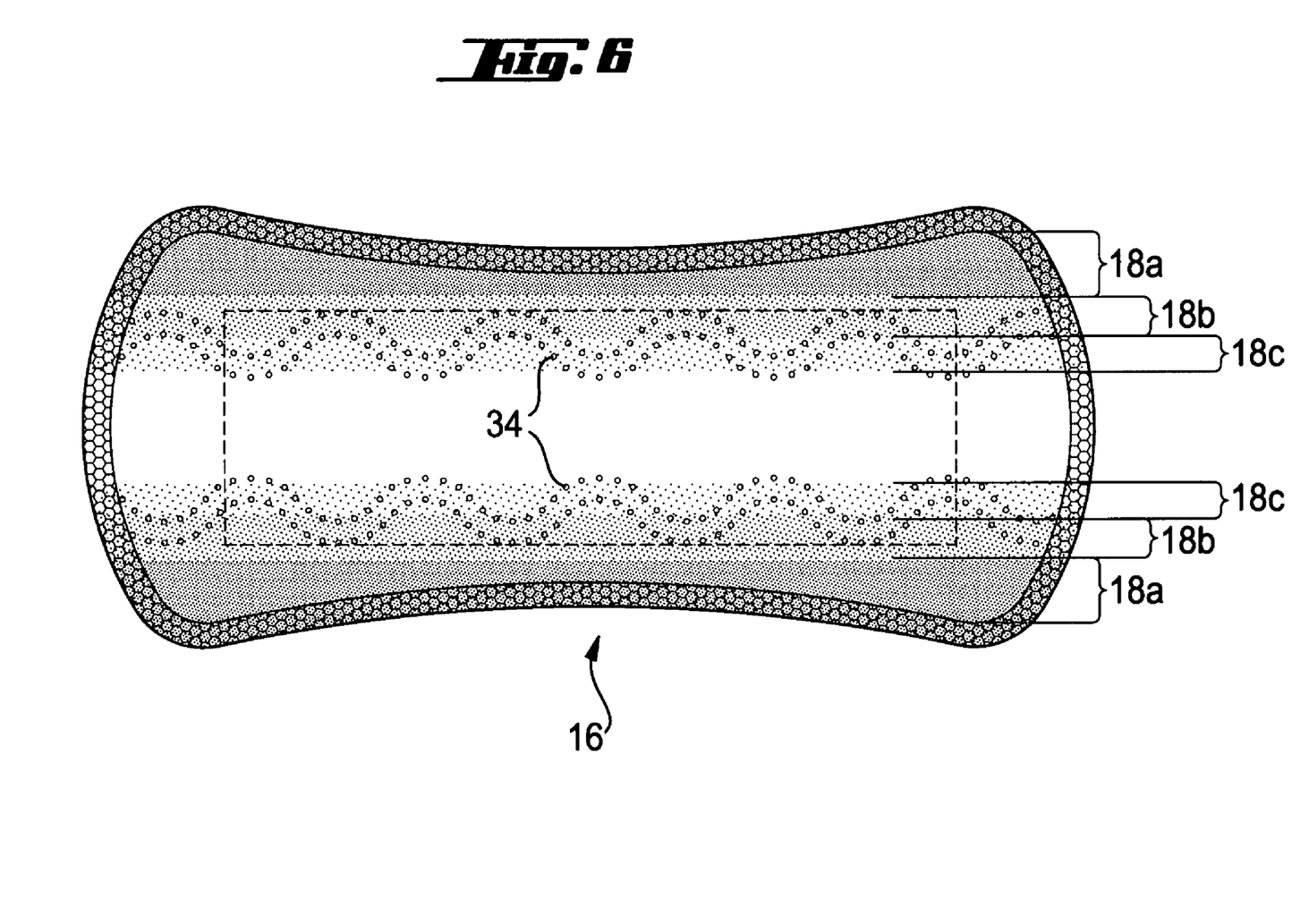
FIG. 6 is a top view of an article according to the invention (e.g. secondary topsheet) on which the ink has been applied in a gradient of print coverage decreasing towards the center of the article.
Figure 7:
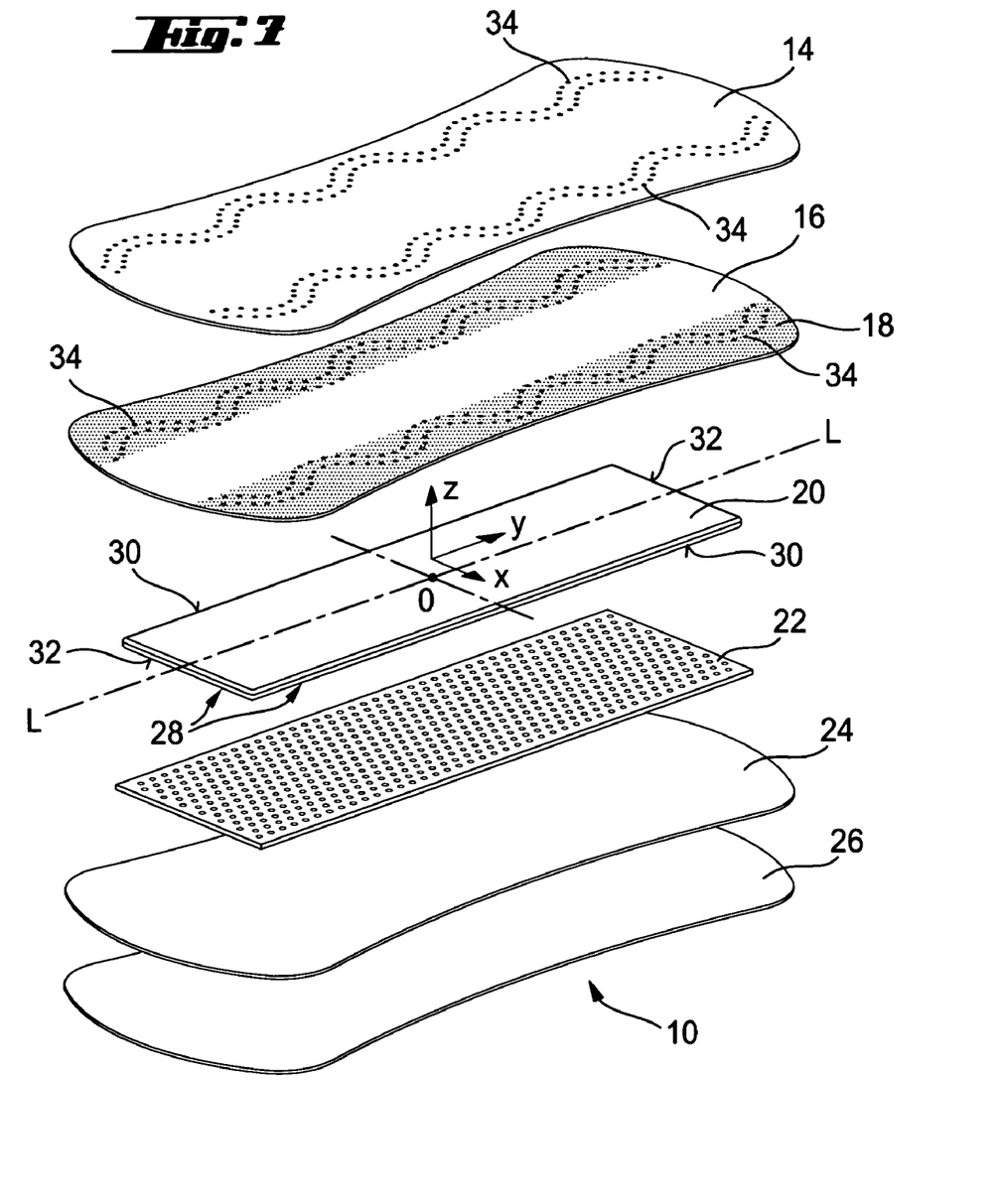
FIG. 7 is an exploded perspective view of a sanitary napkin similar to the napkin of FIG. 1 but without lateral topsheet stripes.

The ink may be applied homogeneously over the whole area of application, or may be applied heterogeneously, for example to display a pre-determined pattern. For example, the percentage of coverage of the ink may generally decreases towards the longitudinal center line of the core, as this may create a gradient of decreasing hydrophobicity pointing towards the center of the core, thus driving the fluid towards the core and this improving the leakage resistance property of the article. Such a gradient is shown in the FIG. 6, wherein the ink application area has been applied with three intensity of coverage: about 100% for the stripe 18a directly adjacent to the longitudinal side edges of the article, about 25% for the stripe 18b next to it and about 10% for the last, most inward, strip 18c. This and other patterns may be applied in one passage of a patterned flexo print or roto gravure apparatus and does not require three different passages.

The layers constituting a sanitary article are normally white or transparent. The ink of the invention is a composition comprising at least one dye or pigment which once applied to the layer of the article will visibly contrast with the rest of the article to provide a visual cue to the user of the improved leakage resistance. The intensity of the dye or pigment contained in the ink can vary from light to strong. If the ink is not applied directly on the top surface of the article, the intermediate layers between the surface of the article and the applied ink are sufficiently transparent so that the ink is at least partially visible through these. The ink may be of any desired colors or shades, including red, green blue, black or even white, as long as the ink is at least partially visible in the finished product. When the ink is applied on the secondary topsheet, the topsheet and, when present, the lateral topsheet stripes are normally sufficiently transparent for this purpose.

The topsheet is the layer of the article which is oriented towards, generally at least partially contacts the body of the wearer, and receives bodily discharges. At least a portion of the topsheet is liquid pervious and should be flexible and nonirritating to the skin. The term "liquid pervious" as used herein refers to components that allow liquids to pass therethrough without significantly retarding or obstructing the transmission of such liquids therethrough. As used herein the term "flexible" refers to materials which are compliant and readily conform to the shape of the body or respond by easily deforming in the presence of external forces. Components are considered absorbent if such components not only transmit such liquids, but also can retain a portion of the liquids deposited on such components.

Any conventional topsheet materials may be used within the invention. Preferably the topsheet is not noisy, to provide discretion for the wearer. The topsheet should be sanitary, clean in appearance and somewhat opaque to hide the bodily discharges collected in and absorbed by the core. Suitable topsheets may be made from nonwoven materials or perforated polyolefinic films.

If desired, the topsheet may include a surfactant to enhance liquid penetration to the core. The surfactant is typically non-ionic and should be nonirritating to the skin. A surfactant density of about 0.01 milligrams per square centimeter of topsheet area is normally suitable. A suitable surfactant is sold by the Glyco Chemical, Inc. of Greenwich, Conn. as Pegosperse 200 ML.

The topsheet may have a plurality of apertures to permit liquids deposited thereon to pass through to the core. An apertured polyolefinic film topsheet having about 5 to about 50 percent open area, typically about 25 percent open area, and a thickness of about 0.01 to about 0.05 millimeters prior to aperturing and about 0.42 to about 0.51 millimeters after aperturing is usual.

The backsheet may be any flexible material and is typically at least partially liquid resistant or liquid impervious. The backsheet prevents discharges collected by and contained in the sanitary napkin, and particularly discharges absorbed by the core, from escaping the sanitary napkin and soiling the clothing and bedding of the wearer. Preferably the backsheet is not noisy, to provide discretion for the wearer. In some executions, a secondary backsheet (discussed below) may be placed intermediate the core and the backsheet to second the backsheet, for example to provide liquid imperviousness.

Any conventional backsheet materials may be used within the invention, such as polyolefinic films. The backsheet may be impervious to malodorous gases generated by absorbed bodily discharges, so that the malodors do not escape and become noticed by the wearer. A low density polyethylene backsheet about 0.01 to about 0.08 millimeters in thickness, preferably about 0.05 millimeters in thickness, is usual. A polyethylene film, such as is sold by the Tredegar Corporation of Terre Haute, Ind., under model X-813 may be used. Further, the backsheet may be made of a soft cloth like material which is hydrophobic relative to the topsheet, e.g., a polyester or polyolefinic fiber backsheet.

The topsheet and the backsheet are preferentially peripherally joined using known techniques, either entirely so that the entire perimeter of the sanitary article is circumscribed by such joinder or are partially peripherally joined at the perimeter. The term "joined" refers to the condition where a first member or component is affixed, or connected, to a second member or component either directly; or indirectly, where the first member or component is affixed, or connected, to an intermediate member or component which in turn is affixed, or connected, to the second member or component. The joined condition between the first member, or component, and the second member, or component, is intended to remain for the life of the sanitary napkin. Conversely, components are considered "removably affixed" if the components may be detached and separated from each other without destruction or unintended gross deformation of either.

Any joined arrangement that provides for capture of the core intermediate the topsheet and the backsheet and a unitary assembly is suitable. Such an assembly has two mutually opposed major faces, one defined by the topsheet and one defined by the backsheet.

The outwardly oriented face of the backsheet may further comprise means for attaching the sanitary napkin to the undergarment of the wearer. Pressure sensitive adhesive has been commonly found to work well for this purpose. A strip of longitudinally oriented adhesive may provide protection against either the front or the back of the sanitary napkin becoming detached from the wearer's undergarment. The adhesive strip may be continuous or intermittent. One arrangement utilizes two longitudinally oriented strips, one on each side of the longitudinal centerline.

The backsheet typically extends across the whole of the absorbent structure and can extend into and form part of or all of the sideflaps, side wrapping elements or wings, when present.

The articles of the invention may comprise a secondary topsheet layer intermediate the topsheet and the absorbent core. Such a secondary layer might be manufactured from a wide range of materials such as woven, nonwoven materials, polymeric materials such as apertured formed thermoplastic films, apertured plastic film, hydro formed thermoplastic films, porous foams, reticulated foams, reticulated thermoplastic films and thermoplastic scrims. Any material described herein before for the topsheet can be used for the secondary layer. In one embodiment, this secondary topsheet layer underlies the apertured topsheet on the entire surface thereof, i.e., the secondary layer extends to the periphery of the topsheet so that the secondary layer underlies the topsheet on the entire inner surface of the topsheet.

The purpose of the secondary topsheet is normally to readily transfer the acquired body fluid from the topsheet to the absorbent core, the transfer of fluid occurring not only vertically in the thickness of the secondary topsheet, but also along the length and the width directions of the absorbent product. This helps the fluid capacity of the underlying storage layer to be fully utilized.

When a secondary topsheet is present, the ink may be applied on the secondary topsheet to improve the barrier effect, especially against re-wetting, because the secondary topsheet normally forms a spacer between the core and the topsheet. In this case, the ink may be applied on either surface (upper or lower) of the topsheet. It may be desirable to apply the ink on the upper surface of the topsheet (as shown in FIG. 3) to make it more visible. Usually the STS is normally sufficiently thin that the ink will be absorbed across the whole thickness of the STS, so that it is not crucial on which surface of the STS the ink is applied.

Figure 8:
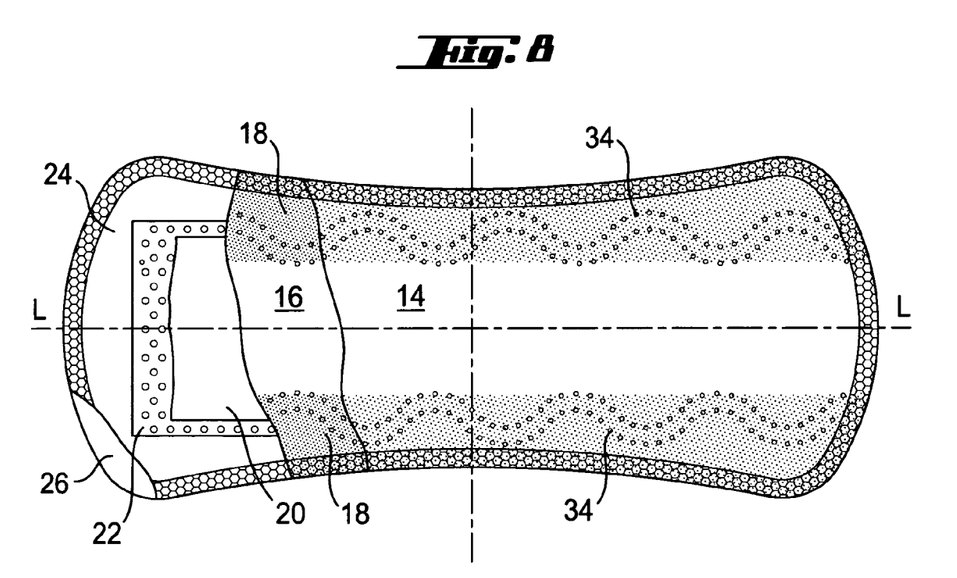
FIG. 8 is a top view, shown partially in cutaway, of the sanitary napkin of FIG. 7.
Figure 9:
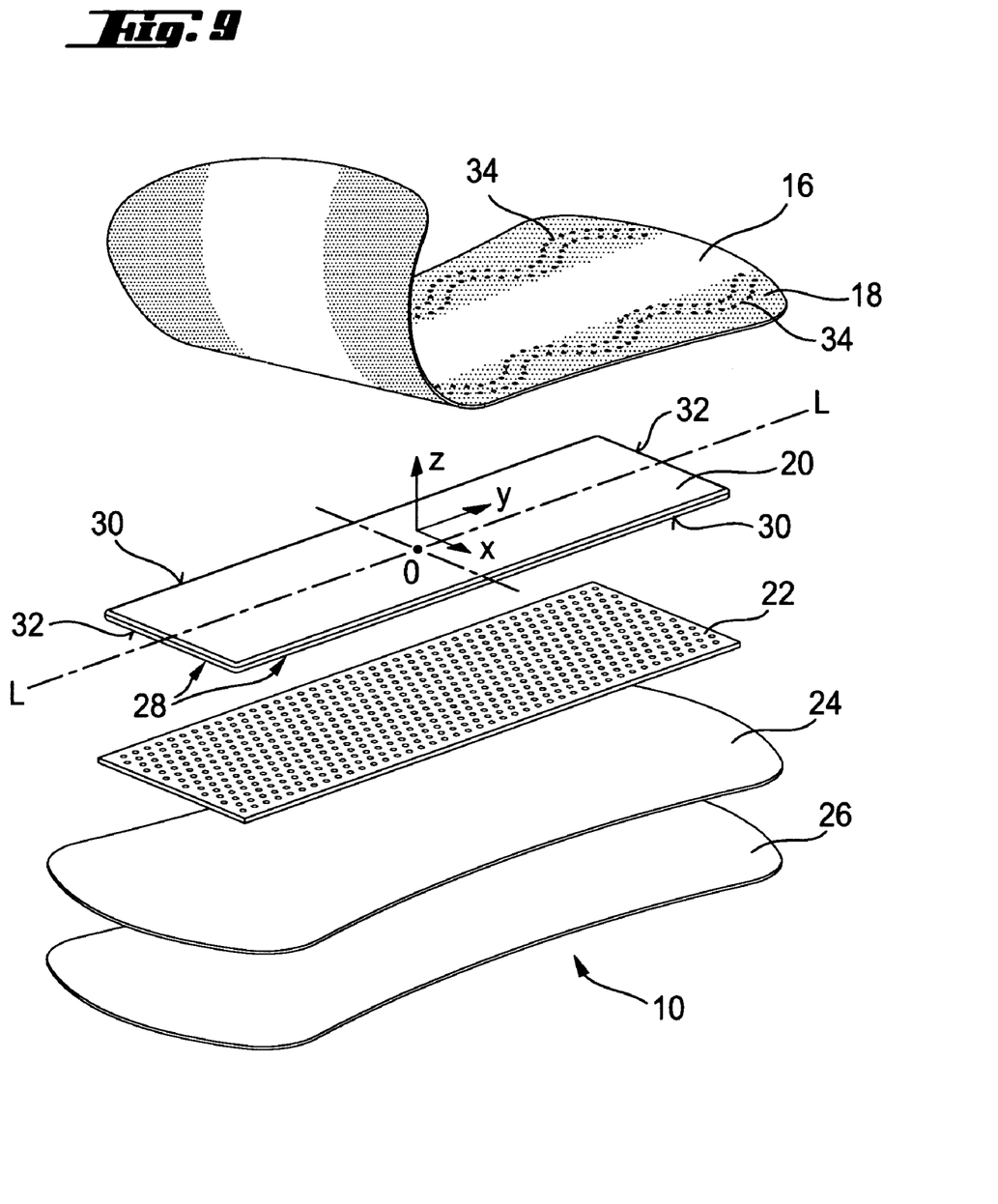
FIG. 9 is an exploded perspective view of a sanitary napkin according to the invention, wherein the ink is applied on the topsheet (no STS is present)
Figure 10:
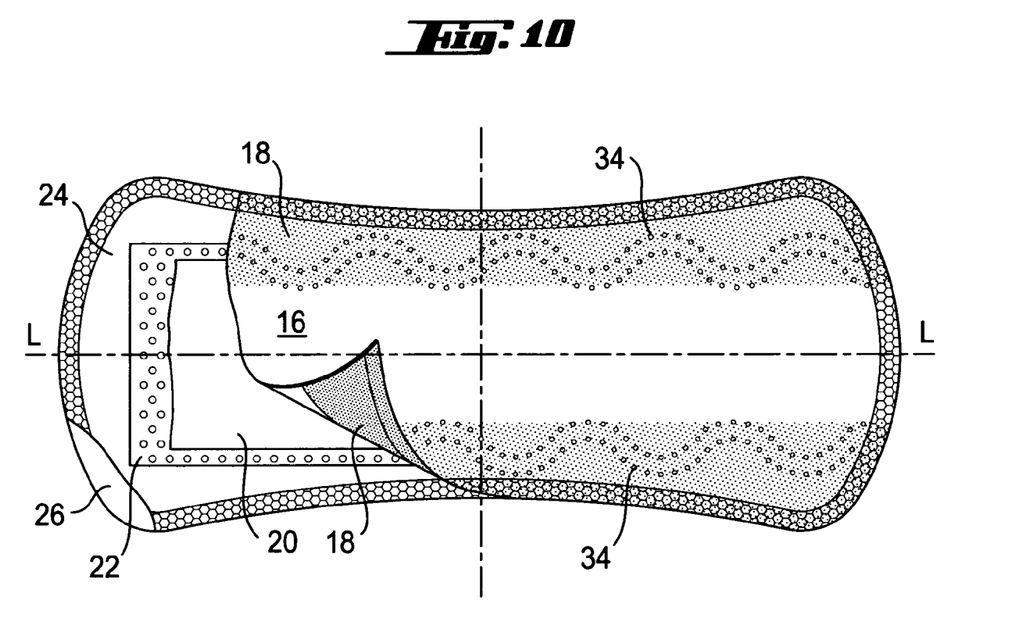
FIG. 10 is a top view, shown partially in cutaway, of the sanitary napkin of FIG. 9.

Although preferred in certain embodiments, the presence of secondary topsheet is however optional, and the ink may be applied on another layer, such as directly on the topsheet, as shown on FIG. 8, or the LTS. However, this may not be acceptable by some because some users do not want to have their skin directly in contact with a dyed topsheet. If the ink is applied on the topsheet, then it may be desirable to apply it on the lower surface of the topsheet for this reason. Although possible, it is normally not desirable to apply the ink directly on the core, at least because the ink may be absorbed by the absorbent material giving uneven result for the application area.

The articles of the invention may comprise nonwoven lateral topsheet stripes placed on top of the topsheet to deliver cloth like, soft feeling of the article edges and improve the aesthetic of the article, for example when these are embossed with a decorative pattern 34 as represented in FIG. 1. These lateral topsheet stripes normally form two parallel stripes extending substantially along the whole length of the longitudinal sides of the article. They can be linear or have any other convenient shape. The presence of the LTS is optional and FIG. 7-10 shows an article without LTS.

The articles of the invention may present an embossing pattern 34 visible at the surface of the article. Embossing normally serves a dual function: first to provide a bonding between the layers, in particular bond the LTS/TS/STS or TS/STS and, second to provide aesthetic performance. The embossing can be achieved with standard techniques such as thermal bond, ultrasonic bond or pressure. A suitable process is thermal bonding wherein the layers are passed through two steel rolls where one is engraved with the visual pattern and the other is flat. Both rolls are warmed to temperature suitable to melt the layer (typical range from about 90 to about 170° C.).

When the ink is applied heterogeneously with a gradient of coverage decreasing towards the centre or centreline of the core, and therefore creates a decreasing gradient of hydrophobicity towards the centre or centreline of the core, it may be desirable that the embossing pattern generally covers this area of heterogeneous application of the ink. This is because the discontinuities or compressed zones (high capillarity) formed by the embossment drive the bodily fluid from the surface of the article towards the core quicker. When the fluid reaches the area of heterogeneous application of the ink, the gradient of hydrophobicity helps driving the fluid towards the centre or centreline of the article, away from the article's edges.

The articles of the invention may comprise a secondary backsheet layer 22 intermediate the absorbent core 20 and the backsheet layer 24. The use of a secondary backsheet is particularly indicated in presence of air permeable backsheet. The purpose of the secondary backsheet is to retard or prevent liquid from passing from the absorbent core to the outside of the product, while allowing free air flow through it. One example of secondary backsheet is a resilient three dimensional polymeric web, which consist of a liquid impervious film which has apertures forming capillarity or cones. The film with capillaries or cone is oriented such us the apex of the cone face the absorbent core this to prevent passage of fluid. In one example, the capillaries or cones can have a slanted shape in order to partly close or completely close when compressed.

If an adhesive is disposed on the other surface of the backsheet, it is typically provided with a protective cover, which is removed prior to use. The protective cover may be a silicone coated release paper, a plastic film or any other easily removable cover. The protective cover may be in a single piece or in a multitude of pieces, e.g. to cover the individual adhesive areas. It also can perform other functions such as providing individualized packaging for the article or provide a disposal function. Any commercially available release paper or film may be used. Suitable examples include BL 30 MG-A SILOX EI/O, BL 30 MG-A SILOX 4 P/O available from Akrosil Corporation, and M&W films available from Gronau in Germany, under the code X-5432.

The dimensions of the sanitary articles should be adapted for the use intended. For example, sanitary napkins are generally smaller and compacter than pads. The sanitary napkin execution of this invention may typically have a caliper of less than about 6 millimeters, or less than about 4 mm, as measured with a comparator gage having an approximately 80.0 gram test weight, an approximately 10.0 gram comparator foot having a diameter of about 2.54 centimeters and a contact surface area of approximately 5.1 square centimeters. Also, the sanitary napkins execution of the present invention may typically have a topsheet surface area of at least about 50 square centimeters to prevent discharged liquids from missing the target area, although some "micro" products may have a smaller surface area (e.g. 30 cm$^2$). The longitudinal center line of the article may be between 10 cm and 25 cm long, and also between 12 cm and 21 cm. All these dimensions are merely indicative and not limitative, because the normal dimensions of these and other types of absorbent sanitary articles may differ, as is known in the art.

The sanitary articles of the present invention may comprise the usual layers or components normally found in commercially available standard articles which may be joined together by standard means such as embossing (e.g. thermal bonding) or gluing or combination of both, and the articles may be produced industrially by conventional means. The fabrication chain may comprise an application step wherein the ink is applied to at least one of the layer of the article. The application step may take place on an isolated layer (e.g. the secondary topsheet) before this layer is joined with any of the other layers, or on the other hand, the ink may be applied on the layer already attached or fixed, entirely or partially, to another layer.

Measurement of the Hydrophobicity of a Substrate

The determination of the Hydrophobicity of a layer can be precisely determined by measuring the Contact Angle formed by a drop of de-ionized water in contact with the surface of the substrate. The method employs a Drop Shape Analysis instrument, such as a Kruss DSA 100, which automatically gently lays drops of water 36 though a syringe 38 (see FIG. 11) on planar and perpendicular substrate samples. The drops have a standardized volume of 6±1 µl. The measurements are made at room temperature (23° C.). This instrument is fitted as standard with a camera and computer with a picture-analysis software. The contact angle is automatically measured according to the Young-Laplace Method. Results are expressed as the average of at least 6 drop contact angle measurements.

Figure 11:
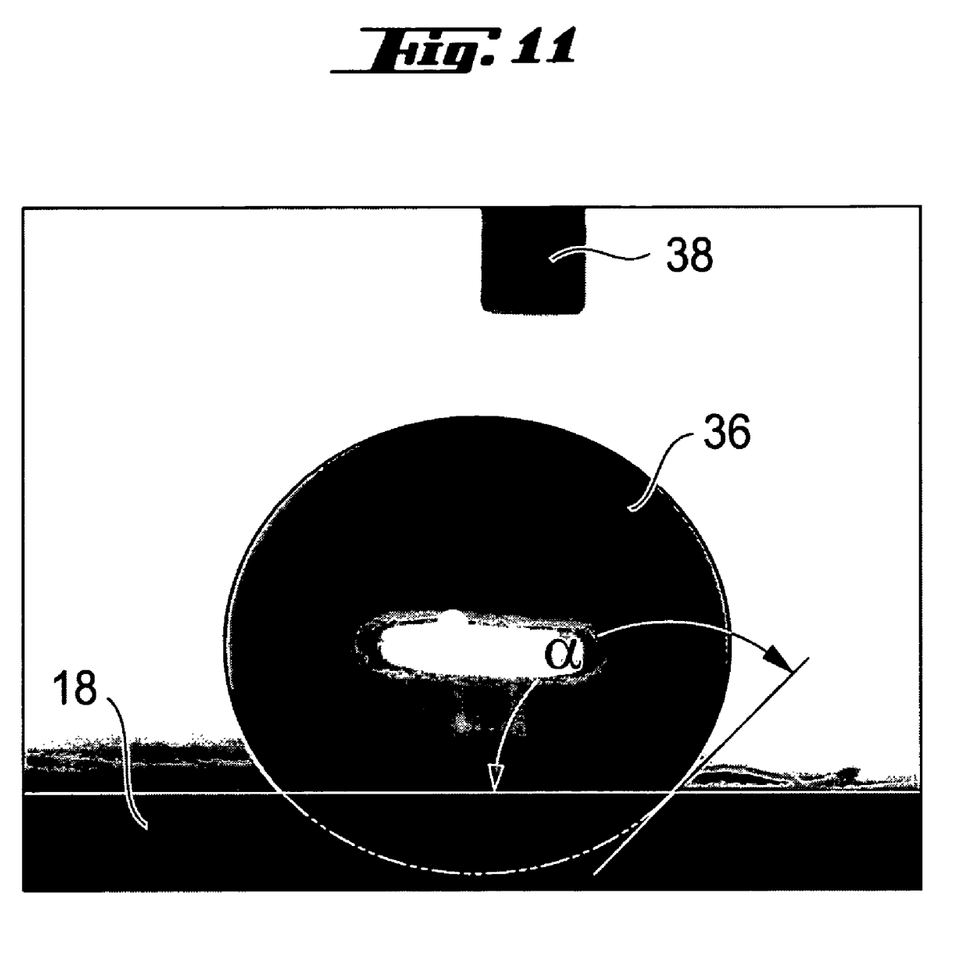
FIG. 11 is a picture of drop of water on a substrate treated with an ink.

The contact angle α in the area in which the ink is applied may measure, according to this method, at least about 60°, at least about 90°. When the percentage of area of coverage is not 100% (so when the area contains areas which are covered by an ink and other areas which are not), the hydrophobicity may be more difficult to measure because the drop behavior may vary depending on the where the drop is laid. For example, if the substrate is inherently hydrophilic and has very low degree of ink coverage (e.g. less than 10%), if the drop is laid on an area of the substrate with no ink it may immediately be absorbed by the substrate. In this case, the drop may be applied on an area with ink coverage, and the hydrophobicity for this area measured. If this covered area is more hydrophobic than the rest of the substrate, then the ink has increased the general hydrophobicity of the substrate. Reporting the hydrophobicity for the total substrate may in this particular case be calculated taken into account the percentage of coverage, for example by using the percentage of coverage as a factor.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent sanitary article made of several layers, said layers including:
   a liquid pervious topsheet;
   a backsheet at least partially peripherally joined to said topsheet;
   an absorbent core disposed between said topsheet and said backsheet, said absorbent core having a periphery; and
   ink disposed on at least one ink application area of a body-facing surface of one of the layers of the article such that the hydrophobicity of the ink application area is increased, wherein the ink application area is partially above the core and extends outwardly across at least a portion of the periphery of the core, but wherein the ink application area does not entirely cover the core, and
   wherein the ink application area is at least partially visible in the finished article.

2. An article according to claim 1 wherein the core has two longitudinal side-edges and wherein the ink application area extends substantially along the whole length of said longitudinal side edges.

3. An article according to claim 2, wherein the width of the ink application area ranges between about 0.4 cm and about 3 cm.

4. An article according to claim 1, wherein the core has two transversal side edges and wherein the ink application area extends substantially along the whole length of the transversal side edges.

5. An article according to claim 1, wherein the article includes a secondary topsheet disposed between the absorbent core and the topsheet, and wherein the ink application area is at least partially disposed on the secondary topsheet.

6. An article according to claim 1, wherein the ink is solvent-based.

7. An article according to claim 1, wherein the ink application area is hydrophobic such that a drop of water deposited on the ink will form an angle $\alpha$ of at least 60°.

8. An article according to claim 1, wherein the article has a longitudinal center line and wherein the length of said article along the longitudinal center line is between about 10 cm and about 25 cm.

9. An article according to claim 1, wherein the article has two longitudinal side edges, and wherein the ink application area extends to said longitudinal side edges.

10. An article according to claim 1, wherein the article is embossed.

11. An article to claim 1, wherein the ink is applied generally homogeneously over the ink application area.

12. An article according to claim 1 wherein the ink is applied heterogeneously over the ink application area.

13. An article according to claim 12 wherein the article has a longitudinal centerline and wherein the gradient of hydrophobicity on the ink application area generally decreases towards the longitudinal center line of the article.

14. An article according to claim 12 wherein the article is embossed and the embossment generally covers the ink application area.

* * * * *